United States Patent
Irla

(10) Patent No.: US 12,146,160 B2
(45) Date of Patent: Nov. 19, 2024

(54) REGULATORY T CELLS TARGETED BY LYMPHOTOXIN ALPHA BLOCKING AGENT AND USES THEREOF

(71) Applicants: INSERM (Institut National de la Santé et de la Recherche Médicale), Paris (FR); Université d'Aix Marseille, Marseilles (FR); Centre National de la Recherche Scientifique (CNRS), Paris (FR)

(72) Inventor: Magali Irla, Marseilles (FR)

(73) Assignees: INSTITUT NATIONAL DE LA SANTE ET DE LA RECHERCHE MEDICALE (INSERM), Paris (FR); UNIVERSITÉ D'AIX MARSEILLE, Marseilles (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 438 days.

(21) Appl. No.: 17/610,325

(22) PCT Filed: May 13, 2020

(86) PCT No.: PCT/EP2020/063346
§ 371 (c)(1),
(2) Date: Nov. 10, 2021

(87) PCT Pub. No.: WO2020/229546
PCT Pub. Date: Nov. 19, 2020

(65) Prior Publication Data
US 2022/0259561 A1    Aug. 18, 2022

(30) Foreign Application Priority Data
May 14, 2019 (EP) .................................... 19305618

(51) Int. Cl.
| | |
|---|---|
| *A61P 37/06* | (2006.01) |
| *A61K 35/17* | (2015.01) |
| *A61P 1/00* | (2006.01) |
| *C07K 14/725* | (2006.01) |
| *C12N 5/0783* | (2010.01) |

(52) U.S. Cl.
CPC ............ *C12N 5/0637* (2013.01); *A61K 35/17* (2013.01); *A61P 1/00* (2018.01); *A61P 37/06* (2018.01); *C07K 14/7051* (2013.01); *C12N 2501/25* (2013.01); *C12N 2510/00* (2013.01)

(58) Field of Classification Search
None
See application file for complete search history.

(56) References Cited

FOREIGN PATENT DOCUMENTS

| WO | 97/03687 A1 | 2/1997 |
| WO | 2017/041002 A1 | 3/2017 |

OTHER PUBLICATIONS

Chiang et al.; "Targeted depletion of lymphotoxin-α-expressing TH1 and TH17 cells inhibits autoimmune disease"; Nature Medicine, vol. 15, No. 7, Jun. 28, 2009, pp. 766-773.
Chiang et al.; "In Vivo Depletion of Lymphotoxin-Alpha Expressing Lymphocytes Inhibits Xenogeneic Graft-versus-Host-Disease"; PLOS One, vol. 7, No. 3, Mar. 12, 2012, e33106.
Goluszko et al.; "Lymphotoxin-alpha deficiency completely protects C57BL/6 mice from developing clinical experimental autoimmune myasthenia gravis"; Journal of Neuroimmunology, vol. 113, No. 1, Feb. 2001, pp. 109-118.
Edinger; "Driving allotolerance: CAR-expressing Tregs for tolerance induction in organ and stem cell transplantation"; Journal of Clinical Investigation, vol. 126, No. 4, Apr. 2016, pp. 1248-1250.
Lopes et al.; "Lymphotoxin a fine-tunes T cell clonal deletion by regulating thymic entry of antigen-presenting cells"; Nature Communications, vol. 9, No. 1262, Mar. 28, 2018, entire document.
Lopes et al.; "Supplementary Information: Lymphotoxin a fine-tunes T cell clonal deletion by regulating thymic entry of antigen-presenting cells"; Nature Communications, vol. 9, No. 1262, Mar. 28, 2018, entire document.
Waldner et al.; "Colitis-associated cancer: the role of T cells in tumor development"; Seminars in Immunopathology, vol. 31, No. 2, Jun. 3, 2009, pp. 249-256.

(Continued)

*Primary Examiner* — Zachary S Skelding
(74) *Attorney, Agent, or Firm* — WC&F IP

(57) ABSTRACT

The present invention relates to regulatory T cell and uses thereof. By their immunosuppressive and anti-inflammatory activities, regulatory T cells play a central role in peripheral tolerance and thus critically prevent the development of autoimmune and inflammatory disorders. The inventors showed that Foxp3+CD4+ Tregs express high levels of LTα, which negatively regulates their immunosuppressive signature. The inventors have demonstrated that the adoptive transfer of Tregs previously incubated with soluble lymphotoxin-β receptor in mice protects from dextran sodium sulfate (DSS)-induced colitis. Thus, the number of cells to be injected in adoptive transfer may be reduced and a transfection or transduction step avoided, which represents a technical facilitation. In particular, the present invention relates to a method of treating or preventing autoimmune disorders and inflammatory-associated cancers in a subject in need thereof comprising the step of administrating to the subject a therapeutically effective amount of regulatory T cells which have been previously incubated with effective amount of soluble lymphotoxin-β receptor.

Figure 1A:
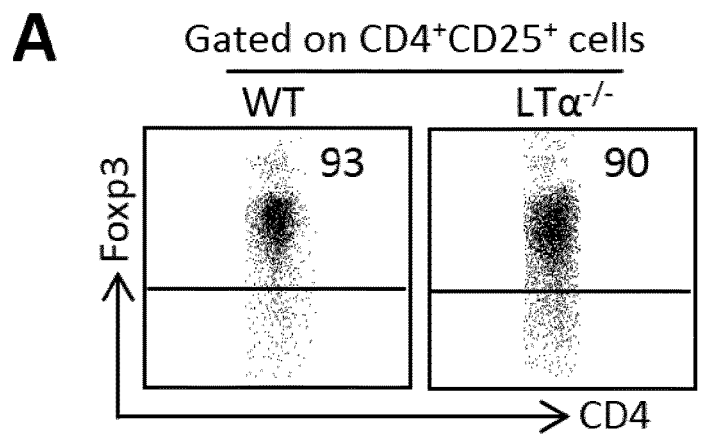

7 Claims, 4 Drawing Sheets
Specification includes a Sequence Listing.

(56) References Cited

OTHER PUBLICATIONS

Bluestone et al.; "The therapeutic potential of regulatory T cells for the treatment of autoimmune disease"; Expert Opinion on Therapeutic Targets, vol. 19, No. 8, Apr. 16, 2015, pp. 1091-1103.
Muzes et al.; "Regulatory T cells in inflammatory bowel diseases and colorectal cancer"; World Journal of Gastroenterology, vol. 18, No. 40, Oct. 28, 2012, pp. 5688-5694.

REGULATORY T CELLS TARGETED BY LYMPHOTOXIN ALPHA BLOCKING AGENT AND USES THEREOF

FIELD OF THE INVENTION

The present invention relates to a method of treating or preventing autoimmune disorders and inflammatory-associated cancers in a subject in need thereof comprising the step of administrating to the subject a therapeutically effective amount of regulatory T cells, wherein the population of regulatory T cells have been previously incubated with an effective amount of lymphotoxin alpha blocking agent.

BACKGROUND OF THE INVENTION

CD4+CD25+Foxp3+ regulatory T cells (Tregs) constitute a subset of CD4+ T cells that plays a critical role in the maintenance of peripheral self-tolerance (1). This cell type possesses the unique ability to immunosuppress hazardous autoreactive T cells that have escaped thymic negative selection and thereby prevents the development of inflammatory and autoimmune disorders. Foxp3+ Treg cells originate from both the thymus and the conversion of nave CD4+ T cells in the periphery and are called natural and induced Tregs, respectively (2). During ontogeny, the development of natural Tregs is substantially delayed compared to that of conventional CD4+ T cells since the first wave of Tregs is generated during the perinatal period whereas conventional CD4+ T cells appear earlier at the embryonic stage (3).

The importance of Foxp3+ Treg cells in the control and maintenance of our immune system was illustrated with scurfy mice that show a mutation in the Foxp3 gene resulting in a truncated non-functional Foxp3 protein (4). These mice die at an early age because they fail to produce thymic-derived Foxp3+ Tregs and thus develop a fatal lymphoproliferative syndrome with multi-organ inflammation. Foxp3 was subsequently identified as the master regulator of Treg development, function and homeostasis. Genetic mutations in the Foxp3 gene have also been identified in humans and are responsible of a severe autoimmune disorder called Immune dysregulation Polyendocrinopathy Enteropathy X-linked (IPEX) syndrome (5). Foxp3+ Tregs use several mechanisms to suppress the immune response (Workman et al., 2009). Four main modes of action have been described: immunosuppressive cytokines (IL-10, TGF-$\beta$ and IL-35), cytolysis of effector T cells and dendritic cells (Granzyme B and A in mice and humans, respectively), metabolic disruption (CD39, CD73 and CD25) and the modulation of antigen presentation in dendritic cells (CTLA-4 and LAG-3).

In mice, the adoptive transfer of WT Tregs in inflammatory bowel disease (IBD) has been shown to prevent and cure established intestinal inflammation (6), type I diabetes (7), experimental autoimmune encephalomyelitis (EAE) (8), and asthma (9). Furthermore, while Treg cells are often protumoral by attenuating tumor immunosurveillance, they in contrast play an antitumoral role in chronic inflammation-mediated cancers by dampening inflammation such as in colitis-associated cancer (CAC) (10). In humans, Treg-based cellular therapy is becoming a reality (11). For example, phase 1 clinical trials using human Tregs have been reported in patients suffering from type I diabetes (12), refractory Crohn's disease (13) or acute graft versus host disease (GVHD) upon stem cell transplantation (14). However, it still a need for developing autoimmune and inflammatory diseases new therapies.

Additionally, it exists a major limiting step on the Treg adoptive transfer technique: a large quantity of cells is required for effective therapy in human. Thus, in the field of Treg cell therapy, it still a need for reducing the required cell numbers to treat efficiently inflammatory and autoimmune disorders.

SUMMARY OF THE INVENTION

By their immunosuppressive and anti-inflammatory activities, Foxp3+CD4+ regulatory T cells (Tregs) play a central role in peripheral tolerance and thus critically prevent the development of autoimmune and inflammatory disorders. The inventors have demonstrated that thymic and splenic Foxp3+CD4+ Tregs express higher levels of lymphotoxin $\alpha$ (LT$\alpha$) than conventional CD4+ T cells, as a membrane anchored LT$\alpha$1$\beta$2 heterocomplex. Thymic and splenic Foxp3+CD4+ Tregs from LT$\alpha^{-/-}$ mice (LT$\alpha^{-/-}$ Tregs) exhibit a signature of highly suppressive cells, indicating that LT$\alpha$ negatively regulates the immunosuppressive functions of this cell type. Interestingly, by limiting bowel inflammation, the adoptive transfer (AT) of LT$\alpha^{-/-}$ Tregs protects from dextran sodium sulfate (DSS)-induced colitis, cures inflammatory bowel disease (IBD) and attenuates the development of colitis-associated cancer (CAC). Importantly, by using mixed bone marrow chimeras, the inventors have found that LT$\alpha$ expression specifically in hematopoietic cells negatively controls the suppressive signature of Tregs. They have identified that LT$\alpha$ negatively regulates the immunosuppressive properties of Tregs and thus could constitute a valuable new target in therapy to increase Treg suppressive activities. They also demonstrated that LT$\alpha$1$\beta$2/LT$\beta$R interactions between Tregs and antigen presenting cells (i.e. dendritic cells and thymic epithelial cells) respectively control the immunosuppressive signature of Tregs. Finally, the inventors found that the AT of regulatory T cells which have been previously incubated with soluble lymphotoxin-$\beta$ receptor (LT$\beta$R) attenuates DSS-induced colitis. By incubating the Tregs with soluble lymphotoxin-$\beta$ receptor, the number of cells to be injected in adoptive transfer may be reduced and a transfection or transduction step avoided, which represents a technical facilitation.

DETAILED DESCRIPTION OF THE INVENTION

A first aspect of the present invention relates to a regulatory T cell which have been previously incubated with effective amount of a lymphotoxin $\alpha$ blocking agent. This incubation with a lymphotoxin-$\alpha$ blocking agent permits to increase the suppressive activity of regulatory T cells.

As used herein, the term "lymphotoxin $\alpha$ blocking agent" refers to an agent that can block LT$\alpha$ ligand binding to LT$\beta$R, eg blocking LT$\alpha$1$\beta$2/LTBR (predominant form) or LT$\alpha$2$\beta$1/LT$\beta$R interaction.

As used herein, the term "lymphotoxin alpha" or "LT$\alpha$" (also known as tumor necrosis factor-beta (TNF-$\beta$)) refers to a member of the tumor necrosis factor family. Lymphotoxin alpha is a cytokine secreted by lymphocytes. Lymphotoxin alpha (Uniprot reference: P01374 for *Homo sapiens*, P09225 for *Mus musculus*) is encoded by the lymphotoxin alpha (LTA) gene (NCBI reference: Gene ID: 4049 for *Homo sapiens*, Gene ID: 16992 for *Mus musculus*). The interaction between LT-$\alpha$ and LT-$\beta$ results in the formation of a membrane bound complex LT$\alpha$1$\beta$2 (predominant form) or LT$\alpha$2$\beta$1/LT$\beta$R which can interact with LT$\beta$R. The inventors shows that blocking the LTα1β2/LTβR interactions permits to increase the suppressive activity of regulatory T cells.

In some embodiment, the lymphotoxin-α blocking agent is a soluble lymphotoxin-β receptor (LTβR).

Thus the invention refers to a regulatory T cell which has been previously incubated with an effective amount of a soluble lymphotoxin-β receptor (LTβR).

As used herein, the term "lymphotoxin-β receptor (LTβR)" has its general meaning in the art and refers to a member of the tumor necrosis factor receptor (TNFR) family. LTβR (Its Uniprot reference: P36941 for *Homo sapiens*, P50284 for *Mus musculus*) is a cell surface receptor for lymphotoxin involved in apoptosis and cytokine release which binds the lymphotoxin membrane form LTα1β2 or LTα2β1 (a complex of lymphotoxin-alpha and lymphotoxin-beta).

A "soluble LTβR," as defined herein, is a polypeptide that includes a lymphotoxin (LT)-binding fragment of the extracellular region of LTβR. For example, a soluble LTβR can include all or a fragment of the extracellular domain of human LTβR. The extracellular domain of human LTβR consist of the amino-acid sequence set forth as the SEQ ID NO:1.

```
SEQ ID NO: 1:
QAVPPYASENQTCRDQEKEYYEPQHRICCSRCPPGTYVSAKCSRIRDTVCA

TCAENSYNEHWNYLTICQLCRPCDPVMGLEEIAPCTSKRKTQCRCQPGMFC

AAWALECTHCELLSDCPPGTEAELKDEVGKGNNHCVPCKAGHFQNTSSPSA

RCQPHTRCENQGLVEAAPGTAQSDTTCKNPLEPLPPEMSGTMLM
```

Soluble forms of the lymphotoxin-β receptors are well known in the art and are disclosed in PCT patent publication WO97/03687. In some embodiments, the LTβR polypeptide is a full-length, immature LTβR polypeptide derived from any species (e.g., any mammal (e.g., a mouse, rat, or monkey). In a preferred embodiment, the LTβR polypeptide is human.

In some embodiment, the soluble LTβR comprises the amino-acid sequence SEQ ID NO:1.

As used herein, "Polypeptide" and "protein" are used interchangeably and mean any peptide linked chain of amino acids, regardless of length or post-translational modification. The LTβR, heterologous polypeptides, or fusion proteins thereof, used in any of the methods of the invention can contain or be human proteins or can be variants that have not more than 50 conservative amino acid substitutions.

As used herein, a "polypeptide fragment" refers to a segment of the polypeptide that is shorter than a full-length, immature polypeptide. A "functional fragment" of a polypeptide has at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100%) of the activity of the mature, polypeptide. Fragments of a polypeptide include terminal as well as internal deletion variants of a polypeptide.

In some embodiments, the LTβR moiety is itself soluble. In some embodiments, the LTβR is joined to a heterologous moiety that increases its solubility, e.g., an Fc region of an immunoglobulin molecule. In some embodiments, the heterologous moiety can be covalently joined to the LTβR moiety.

In some embodiments, the soluble LTβR can be modified by covalent attachment of a second polypeptide moiety, e.g., a heterologous polypeptide (e.g., to make an LTβR fusion protein) or a non-polypeptide moiety.

In some cases, such moieties can improve a pharmacodynamic or pharmacokinetic parameter, such as solubility or half-life. LTβR fusion proteins can include all or part of the constant region of an antibody (e.g., an Fc domain), transferrin, or albumin, such as human serum albumin (HSA) or bovine serum albumin (BSA). The fusion protein can include a linker region between the LTβR sequence and the non-LTβR protein domain. In some embodiments, a soluble LTβR is modified by covalent attachment to a polymer such as a polyethylene glycol (PEG). While not limited by any particular theory or mechanism, such soluble LTβR can act as decoy receptors to reduce (block or neutralize) LTβR activity.

In some embodiment, the LTβR fusion protein has the LTβR extracellular ligand binding domain fused to an immunoglobulin constant heavy chain domain. More preferably, the LTβR ligand binding domain is fused to a human IgG Fc domain.

The term "Fc domain" of an antibody refers to a part of the molecule comprising the hinge, CH2 and CH3 domains, but lacking the antigen binding sites. The term is also meant to include the equivalent regions of an IgM or other antibody isotype.

In some embodiment, the soluble LTβR is baminercept. Baminercept is a lymphotoxin beta receptor antagonist developed by Biogen Idec. Its CAS number is 909110-25-4 and its amino acid sequence consist of SEQ ID NO:2.

In some embodiment, the soluble LTβR protein comprises the amino acid sequence SEQ ID NO:2.

```
SEQ ID NO: 2:
AVPPYASENQTCRDQEKEYYEPQHRICCSRCPPGTYVSAKCSRIRDTVCAT

CAENSYNEHWNYLTICQLCRPCDPVMGLEEIAPCTSKRKTQCRCQPGMFCA

AWALECTHCELLSDCPPGTEAELKDEVGKGNNHCVPCKAGHFQNTSSPSAR

CQPHTRCENQGLVEAAPGTAQSDTTCKNPLEPLPPEMSGTMVDKTHTCPPC

PAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALH

NHYTQKSLSLSPG
```

In some embodiment, the lymphotoxin alpha blocking agent is an anti-LTα blocking antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

As used herein, "anti-LTα blocking antibody" refers to an anti-LTα antibody that prevents other antibodies or receptor from combining with LT-α. The anti-LTα blocking antibody prevent the LTα1β2/LTβR or LTα2β1/LTβR interactions.

Examples of anti-LTα blocking antibodies include the following ones:
  Abcam: clones AT15A3 and AB197677
  Thermo Fischer: Clone PAS-82314
  R&D Systems: Clone: 135125 (Monoclonal, IgG1)
  MBL International: Clone #1 (Monoclonal, IgG1)
  GeneTex: Clone 12B4 (Monoclonal, IgG1)
  LifeSpan BioSciences: Catalog Number LS-C18337-100 (Monoclonal, IgG2b)
  United States Biological: Clone 9B9 (Monoclonal, IgG1)
  Novus Biologicals: Clone MM0575-7U9 (Monoclonal, IgG1)
  MyBioSource.com: Clone #12B4 (Monoclonal, IgG1)
  MyBioSource.com: Clone #3F11 (Monoclonal, IgG1)
  Creative Biolabs: Clone 359-238-8 (Monoclonal, IgG1)
  Creative Biolabs: Clone 3F12.2D3 (Monoclonal, IgG1)
  Creative Diagnostics: Clone 460-349-9 (Monoclonal, IgG1)

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of LTα. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in LTα. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementary determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., /. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb. The term "VHH" refers to the single heavy chain having 3 complementarity determining regions (CDRs): CDR1, CDR2 and CDR3. The term "complementarity determining region" or "CDR" refers to the hypervariable amino acid sequences which define the binding affinity and specificity of the VHH.

The VHH according to the invention can readily be prepared by an ordinarily skilled artisan using routine experimentation. The VHH variants and modified form thereof may be produced under any known technique in the art such as in-vitro maturation.

VHHs or sdAbs are usually generated by PCR cloning of the V-domain repertoire from blood, lymph node, or spleen cDNA obtained from immunized animals into a phage display vector, such as pHEN2. Antigen-specific VHHs are commonly selected by panning phage libraries on immobilized antigen, e.g., antigen coated onto the plastic surface of a test tube, biotinylated antigens immobilized on streptavidin beads, or membrane proteins expressed on the surface of cells. However, such VHHs often show lower affinities for their antigen than VHHs derived from animals that have received several immunizations. The high affinity of VHHs from immune libraries is attributed to the natural selection of variant VHHs during clonal expansion of B-cells in the lymphoid organs of immunized animals. The affinity of VHHs from non-immune libraries can often be improved by mimicking this strategy in vitro, i.e., by site directed mutagenesis of the CDR regions and further rounds of panning on immobilized antigen under conditions of increased stringency (higher temperature, high or low salt concentration, high or low pH, and low antigen concentrations). VHHs derived from camelid are readily expressed in and purified from the *E. coli* periplasm at much higher levels than the corresponding domains of conventional antibodies. VHHs generally display high solubility and stability and can also be readily produced in yeast, plant, and mammalian cells. For example, the "Hamers patents" describe methods and techniques for generating VHH against any desired target (see for example U.S. Pat. Nos. 5,800,988; 5,874,541 and 6,015,695). The "Hamers patents" more particularly describe production of VHHs in bacterial hosts such as *E. coli* (see for example U.S. Pat. No. 6,765,087) and in lower eukaryotic hosts such as moulds (for example *Aspergillus* or *Trichoderma*) or in yeast (for example *Saccharomyces, Kluyveromyces, Hansenula* or *Pichia*) (see for example U.S. Pat. No. 6,838,254).

As used herein, the term "regulatory T cells" or "Tregs" refers to a subpopulation of T cells which modulates the immune system, maintains tolerance to self-antigens, and abrogates autoimmune and inflammatory diseases. These cells generally suppress or downregulate induction and proliferation of effector T cells and modulate antigen presenting cell function. Tregs are cells capable of suppressive activity (i.e. inhibiting proliferation of conventional T cells), either by cell-cell contact or through the release of immunosuppressive cytokines.

Another object of the present invention relates to a population of regulatory T cells of the invention.

As used herein, the term "population" refers to a population of cells, wherein the majority (e.g., at least about 50%, preferably at least about 60%, more preferably at least about 70%, and even more preferably at least about 80%) of the total number of cells have the specified characteristics of the cells of interest and express the markers of interest.

Another object of the present invention relates to an ex vivo method for stimulating regulatory T cells immunosuppressive activity, said method comprising:
i) Obtaining a biological sample from a subject;
ii) Isolating regulatory T cells from said sample;
iii) In vitro expansion of regulatory T cells
iv) Incubating said isolated regulatory T cells with effective amount of lymphotoxin alpha blocking agent, such as a soluble lymphotoxin-β receptor (LTβR), in order to block LTα1β2/LTβR or LTα2β1/LTβR interactions.

As used herein, the term "subject" denotes a mammal, such as a rodent, a feline, a canine, and a primate. Preferably, a subject according to the invention is a human.

As used herein, the term "biological sample" refers to any body fluid or tissue. In one embodiment, the biological sample is blood sample.

As used herein, the term "regulatory T cell immunosuppressive activity" is well-known in the art and refers to the ability of Tregs to suppress or downregulate induction and proliferation of effector T cells. As used herein the term "stimulating regulatory T cells immunosuppressive activity" refers to an increase of regulatory T cell immunosuppressive activity.

As used herein, "isolating" refers to removal of a cell or a cell population from its natural environment. As used herein, "isolated" refers to a cell or a cell population that is removed from its natural environment (such as the blood sample) and that is isolated, purified or separated, and is at least about 75% free, 80% free, 85% free and preferably about 90%, 95%, 96%, 97%, 98%, 99% free, from other cells with which it is naturally present.

According to the method of the present invention, the regulatory T cells of the invention are isolated from the sample. All the techniques known by the skilled man may be used. In one embodiment, the regulatory T cells are isolated by cell sorter after pre-enrichment of CD4$^+$ T cells by depletion of CD8$^+$ and CD19$^+$ cells. The purity of sorted regulatory T cells was >97%.

A further object of the present invention relates to the regulatory T cell pre-incubated of the invention characterized in that it expresses a TCR or a chimeric antigen receptor which recognizes/binds to an autoantigen.

As used herein, the term "TCR" has its general meaning in the art and refers to the molecule found on the surface of T cells that is responsible for recognizing antigens bound to MHC molecules. In particular "a T cell characterized in that it expresses a TCR" means that a T cell was genetically engineered for expressing said TCR by e.g. transfecting or transducing said T cell in vitro or ex vivo with a nucleic acid molecule encoding said TCR.

As used herein, the term "Chimeric Antigen Receptor" or "CAR" has its general meaning in the art and refers to an artificially constructed hybrid protein or polypeptide containing the antigen binding domains of an antibody (e.g., scFv) linked to T-cell signaling domains. In the context of the invention, the antigen binding domains of the antibody recognizes/binds to an autoantigen.

As used herein, the term "recognizes" or "binds" means in the context of the invention that the TCR or the chimeric antigen receptor has affinity for an antigen.

As used herein, the term "autoantigen" refers to an endogenous antigen, or an active fragment thereof, that is recognized by the immune system. Auto-antigens comprise, but are not limited to, cellular proteins, phosphoproteins, cellular surface proteins, cellular lipids, nucleic acids, glycoproteins, including cell surface receptors. Examples of auto-antigens include but are not limited to preproinsulin (PPI), glutamic acid decarboxylase (GAD), insulinoma-associated protein 2 (IA-2), islet-specific glucose-6-phosphatase catalytic-subunit-related protein (IGRP), zinc transporter 8 (ZnT8) and chromogranin A for T1D; myeloperoxydase and proteinase 3 for granulomatosis with polyangiitis; myelin oligodendrocyte glycoprotein (MOG) and myelin basic protein (MBP) in multiple sclerosis; and gliadins in celiac disease.

Another object relates to a population of regulatory T cells of the invention and which expresses a TCR or a chimeric antigen receptor recognizing/binding to an autoantigen.

In one embodiment, the regulatory T cells of the invention have been transfected or transduced in vitro or ex vivo with a vector, encoding for the chimeric antigen receptor or the antigen-specific TCR to expresses a chimeric antigen receptor or an antigen-specific TCR which recognizes/binds to an autoantigen. Thus, another object of the present invention relates to a method of producing the regulatory T cell of the invention expressing a chimeric antigen receptor or an antigen-specific TCR which recognizes/binds to an autoantigen, which comprises the step of transfecting or transducing a regulatory T cell of the invention in vitro or ex vivo with a vector encoding for the chimeric antigen receptor or the antigen-specific TCR.

The term "transduction" or "transducing" refers to the viral transfer of genetic material and its expression in a recipient cell.

The term "transfection" or "transfecting" as used herein refers to the process of introducing DNA (e.g., formulated DNA expression vector) into a cell, thereby, allowing cellular transformation.

As used herein, the term "vector" refers to a nucleic acid molecule allowing insertion of foreign nucleic acid without disrupting the ability of the vector to replicate and/or integrate in a host cell.

The regulatory T cells populations of the present invention (population of regulatory T previously incubated with effective amount of a lymphotoxin alpha blocking agent, such as soluble lymphotoxin-β receptor (LTβR), and which expresses or not a TCR or a chimeric antigen receptor recognizing/binding to an autoantigen) are particularly suitable for therapeutic uses.

A further object of the present invention relates to a population of regulatory T which have been previously incubated with effective amount of a lymphotoxin alpha blocking agent and which expresses or not a TCR or a chimeric antigen receptor recognizing/binding to an autoantigen for use in adoptive cell therapy.

The term "adoptive cell therapy" as used herein refers to a cell-based immunotherapy that relates to the transfusion of autologous or allogenic lymphocytes, genetically modified or not.

The populations of Treg of the present invention can be utilized in methods and compositions for adoptive cell therapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the age and weight of the recipient, on the severity of the targeted condition. Classically, the number of Treg to be injected is about $1$-$3 \times 10^6$/kg (Adair et al. Human Tregs Made Antigen Specific by Gene Modification: The Power to Treat Autoimmunity and Anti-drug Antibodies with Precision. Front Immunol 2017). However, the dosage may be reduced when using the Treg of the invention because their immunosuppressive activity is increased. In one embodiment, the dosage may be reduced at least by 50%. In one embodiment, the dosage may be reduced by 75%. In one embodiment, the standard cell therapy dosages may be used: these amount of cells may be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. The clinically relevant number of immune cells can be apportioned into multiple infusions that cumulatively equal or exceed the desired total amount of cells.

For the purpose of the invention, the regulatory T cell of the present invention and used in the adoptive cell therapy may be isolated from the subject ("autologous cells") or from another individual ("allogeneic cells").

As used herein, "allogeneic cells" refers to cells isolated from one subject (the donor) an infused in another (the recipient or host).

As used herein, "autologous cells" refers to cells that are isolated and infused back into the same subject (recipient or host).

In one embodiment, the regulatory T cells of the present invention and used in the adoptive cell therapy may derived from stem cells.

The terms "stem cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.).

In a particular embodiment, the regulatory T cells of the present invention and used in the adoptive cell therapy may derived from induced pluripotent stem cells.

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

In a particular embodiment, the regulatory T cells of the invention and used in the adoptive cell therapy may derived from embryonic stem cells.

The term "embryonic stem cell" as used herein refers to naturally occurring pluripotent stem cells of the inner cell mass of the embryonic blastocyst (see, for e.g., U.S. Pat. Nos. 5,843,780; 6,200,806; 7,029,913; 7,584,479, which are incorporated herein by reference). Such cells can similarly be obtained from the inner cell mass of blastocysts derived from somatic cell nuclear transfer (see, for example, U.S. Pat. Nos. 5,945,577; 5,994,619; 6,235,970, which are incorporated herein by reference). Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent.

In one embodiment, the regulatory T cells of the present invention and used in the adoptive cell therapy may derived from the conversion of conventional CD4+ T cells.

A further object of the present invention refers to a method of treating or preventing an autoimmune disorders comprising administering to a patient in need thereof an effective amount of lymphotoxin alpha blocking agent to stimulate regulatory T cells immunosuppressive activity. More particularly, the present invention refers to a method of treating or preventing autoimmune disorders or inflammatory-associated cancers in a subject in need thereof comprising the step of administrating to the subject a therapeutically effective amount of population of regulatory T cells, wherein the population of regulatory T cells have been previously incubated with effective amount of lymphotoxin alpha blocking agent. This incubation with a lymphotoxin alpha blocking agent permits to increase the suppressive activity of regulatory T cells.

In one embodiment, the lymphotoxin alpha blocking agent is a soluble lymphotoxin-β receptor (LTβR).

In one embodiment, the regulatory T cells express a TCR or a chimeric antigen receptor which recognizes/binds to an autoantigen.

In some embodiment, the regulatory T cells do not express a TCR or a chimeric antigen receptor which recognizes/binds to an autoantigen.

Thus, the present invention refers to a method of treating or preventing autoimmune disorders in a subject in need thereof comprising the step of administrating to the subject a therapeutically effective amount of the population of regulatory T cells which have been pre-incubated with effective amount of soluble LTβR and/or the population of regulatory T cells which have been pre-incubated with effective amount of soluble LTβR and that it expresses a TCR or a chimeric antigen receptor which recognizes/binds to an autoantigen.

As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system, in concert with cells of the innate immune system, responds to self-antigens and mediates cell and tissue damage. In some embodiments, autoimmune diseases are characterized as being a result of, at least in part, a humoral and/or cellular immune response. Examples of autoimmune disease include, without limitation, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal and neuronal neuropathies, Behcet's disease, bullous pemphigoid, autoimmune cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), autoimmune neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis [Granulomatosis with Polyangiitis (GPA)]. In some embodiments, the autoimmune disease is selected from the group consisting of rheumatoid arthritis, type 1 diabetes, systemic lupus erythematosus (lupus or SLE), myasthenia gravis, multiple sclerosis, scleroderma, Addison's Disease, bullous pemphigoid, pemphigus vulgaris, Guillain-Barré syndrome, Sjogren syndrome, dermatomyositis, thrombotic thrombocytopenic purpura, hypergammaglobulinemia, monoclonal gammopathy of undetermined significance (MGUS), Waldenstrom's macroglobulinemia (WM), chronic inflammatory demyelinating polyradiculoneuropathy (CIDP), Hashimoto's Encephalopathy (HE), Hashimoto's Thyroiditis, Graves' Disease, Wegener's Granulomatosis [Granulomatosis with Polyangiitis (GPA)].

In one embodiment, the autoimmune disease is inflammatory bowel disease.

In one embodiment, the autoimmune disease is multiple sclerosis or type 1 diabetes.

A further object of the present invention relates to a method of treating or preventing inflammation-associated cancer in a subject in need thereof comprising the step of administrating to the subject a therapeutically effective amount of regulatory T cells wherein the population of regulatory T cells have been previously incubated with effective amount of lymphotoxin alpha blocking agent.

In some embodiment the lymphotoxin alpha blocking agent is a soluble lymphotoxin-β receptor (LTβR).

As used herein, the term "inflammation-associated cancer" refers to any cancer for which inflammation is considered to be at least one of the pathogenesis mechanisms involved in cancer initiation and development. Examples of inflammation-associated cancer include, but it is not limited to, colitis-associated cancer, gastric adenocarcinoma, bladder carcinoma, liver carcinoma, rectal carcinoma, cholangiocarcinoma, colon carcinoma, colorectal carcinoma, Gall bladder cancer, hepatocellular carcinoma, ovarian carcinoma, cervical carcinoma, skin carcinoma, esophageal carcinoma, bladder cancer, mesothelioma, lung cancer, oral squamous cell carcinoma, pancreatic carcinoma, vulvar squamous cell carcinoma, salivary gland carcinoma, lung carcinoma, MALT lymphoma.

In one embodiment, the inflammation-associated cancer is colitis-associated cancer. The colitis-associated cancer is a subtype of colorectal cancer.

A further object of the present invention relates to a method of treating or preventing allergy in a subject in need thereof comprising the step of administrating to the subject a therapeutically effective amount of regulatory T cells wherein the population of regulatory T cells has been previously incubated with effective amount of lymphotoxin alpha blocking agent.

In some embodiment the lymphotoxin alpha blocking agent is a soluble lymphotoxin-β receptor (LTβR).

As used herein, the term "allergy" generally refers to an inappropriate immune response characterized by inflammation and includes, without limitation, food allergies, respiratory allergies and other allergies causing or with the potential to cause a systemic response such as, by way of example, Quincke's oedema and anaphylaxis. The term encompasses allergy, allergic disease, hypersensitive associated disease or respiratory disease associated with airway inflammation, such as asthma or allergic rhinitis. In some embodiments, the method of the present invention is effective in preventing, treating or alleviating one or more symptoms related to anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD). Hypersensitivity associated diseases or disorders that may be treated by the method of the present invention include, but are not limited to, anaphylaxis, drug reactions, skin allergy, eczema, allergic rhinitis, urticaria, atopic dermatitis, dry eye disease [or otherwise referred to as Keratoconjunctivitis sicca (KCS), also called keratitis sicca, xerophthalmia], allergic contact allergy, food allergy, allergic conjunctivitis, insect venom allergy and respiratory diseases associated with airway inflammation, for example, IgE mediated asthma and non-IgE mediated asthma. The respiratory diseases associated with airway inflammation may include, but are not limited to, rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD).

A further object of the present invention relates to a method of treating or preventing immune reactions against molecules that are exogenously administered in a subject in need thereof comprising the step of administrating to the subject a therapeutically effective amount of regulatory T cells wherein the population of regulatory T cells have been previously incubated with effective amount of lymphotoxin alpha blocking agent.

In some embodiment the lymphotoxin alpha blocking agent is a soluble lymphotoxin-β receptor (LTβR).

Non-limiting examples of this kind include immune reactions against replacement therapeutics in the context of genetic deficiencies, which include, but are not limited to, haemophilia A, haemophilia B, congenital deficiency of other clotting factors such as factor II, prothrombin and fibrinogen, primary immunodeficiencies (e.g. severe combined immunodeficiency, X-linked agammaglobulinemia, IgA deficiency), primary hormone deficiencies such as growth hormone deficiency and leptin deficiency, congenital enzymopathies and metabolic disorders such as disorders of carbohydrate metabolism (e.g. sucrose-isomaltase deficiency, glycogen storage diseases), disorders of amino acid metabolism (e.g. phenylketonuria, maple syrup urine disease, glutaric acidemia type 1), urea cycle disorders (e.g. carbamoyl phosphate synthetase I deficiency), disorders of organic acid metabolism (e.g. alcaptonuria, 2-hydroxyglutaric acidurias), disorders of fatty acid oxidation and mitochondrial metabolism (e.g. medium-chain acyl-coenzyme A dehydrogenase deficiency), disorders of porphyrin metabolism (e.g. porphyrias), disorders of purine or pyrimidine metabolism (e.g. Lesch-Nyhan syndrome), disorders of steroid metabolism (e.g. lipoid congenital adrenal hyperplasia, congenital adrenal hyperplasia), disorders of mitochondrial function (e.g. Kearns-Sayre syndrome), disorders of peroxisomal function (e.g. Zellweger syndrome), lysosomal storage disorders (e.g. Gaucher's disease, Niemann Pick disease).

A further object of the present invention relates to a method of treating or preventing immune reactions against a grafted tissue or grafted cells in a subject in need thereof comprising the step of administrating to the subject a therapeutically effective amount of regulatory T cells wherein the population of regulatory T cells have been previously incubated with effective amount of lymphotoxin alpha blocking agent.

In some embodiment the lymphotoxin alpha blocking agent is a soluble lymphotoxin-β receptor (LTβR).

As used herein, the term "grafted" refers to organs and/or tissues and/or cells which can be obtained from a first organism (or donor) and transplanted into a second organism (or recipient). Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the present invention is also particularly suitable for preventing or suppressing an immune response associated with rejection of a donor tissue, cell, graft, or organ transplant by a recipient subject. Graft-related diseases or disorders include graft versus host disease (GVHD), such as associated with bone marrow transplantation, and immune disorders resulting from or associated with rejection of organ, tissue, or cell graft transplantation (e.g., tissue or cell allografts or xenografts), including e.g., grafts of skin, muscle, neurons, islets, organs, parenchymal cells of the liver, etc. Thus the method of the invention is useful for preventing Host-Versus-Graft-Disease (HVGD) and Graft-Versus-Host-Disease (GVHD). The chimeric construct may be administered to the subject before, during and/or after transplantation (e.g., at least one day before transplantation, at least one day after transplantation, and/or during the transplantation procedure itself). In some embodiments, the chimeric construct may be administered to the subject on a periodic basis before and/or after transplantation.

As used herein, the term "subject" denotes a mammal, such as a rodent, a feline, a canine, and a primate. Preferably, a subject according to the invention is a human.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" or "preventing" refers to the reduction in the risk of acquiring or developing a given condition.

As used herein the terms "administering" or "administration" refer to the act of injecting or otherwise physically delivering a substance as it exists outside the body into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

The "therapeutically effective amount" is determined using procedures routinely employed by those of skill in the art such that an "improved therapeutic outcome" results. It will be understood, however, that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination; and like factors well known in the medical arts. Accordingly to the invention, the regulatory T cells can be incubated over a wide range from 1 to 500 µg/ml of soluble lymphotoxin-β receptor (LTβR) for a wide range of time from 5 to 120 minutes. Thus the regulatory T cells can be incubated with 1, 2, 5, 10, 30, 50, 100, 150, 200 or 500 µg/ml for 5, 10, 30, 60, 90 or 120 min.

In some embodiment, the regulatory T cells have been incubated with 50 µg/ml of soluble lymphotoxin-β receptor (LTβR) for 30 min.

While the innate immune system is well known to be involved in the tissue healing process, the adaptive immune system has recently emerged as a key player. T-cells, in particular, regulatory T-cells (Treg), have been shown to promote repair and regeneration of various organ systems (15). Thus, a further object of the present invention relates to a population of regulatory T which have been previously incubated with effective amount of a lymphotoxin alpha blocking agent and which expresses or not a TCR or a chimeric antigen receptor recognizing/binding to an autoantigen for use in regenerative therapy.

As used herein, the term "regenerative therapy" refers to the process of regenerating human or animal cells, tissues or organs to restore or establish normal function. Regenerative medicine has the potential to heal or replace tissues and organs damaged by age, disease, or trauma, as well as to normalize congenital defects This field holds the promise of engineering damaged tissues and organs by stimulating the body's own repair mechanisms to functionally heal previously irreparable tissues or organs.

Regenerative therapy include but are not limited to tissue healing process such as skin regeneration and organ regeneration such as cardiac regeneration, liver regeneration, kidney regeneration, pancreas regeneration, lung regeneration, hair-follicle regeneration, heart regeneration; bladder regeneration; muscle regeneration (such as skeletal muscle regeneration and heart muscle regeneration), bone regeneration, and central nervous system regeneration.

In some embodiment, regenerative therapy is muscle regeneration, skin regeneration, bone regeneration or central nervous system regeneration.

As used, the term "organ or tissue regeneration" refers to reinitiating the proliferative activity of differentiated resident cells in the organ or tissue and to replace their profuse loss of cells after the organ injury.

As used herein, the term "organ injury" has its general meaning in the art and refers any kind of reversible or irreversible damage to the organ's cells. Organ injury may be caused by any condition. Typical organ injury includes ablative therapy (e.g. required to prepare patients to bone marrow transplantation (BMT) for example), complications related to HIV/AIDS, aging process, malnutrition, and radiation poisoning. The term also includes age-related involution, i.e. the progressive shrinking of the organ with age. Organ injury, such as thymic injury, may result from irradiation, for instance as medical treatment. Examples of diseases which are in part treated with irradiation included but are not limited to: cancers such as multiple myeloma, non-Hodgkin's lymphoma, Hodglin's disease, acute myeloid leukemia, neuroblastoma, ovarian cancer, germ-cell tumors, acute lymphoblastic leukemia, chronic myeloid leukemia, myelodysplasic syndromes, myeloproliferative disorders, chronic lymphocytic leukemia, juvenile chronic myeloid leukemia, and others diseases such as autoimmune disorders, amyloidosis, aplastic anemia, paroxysmal nocturnal hemoglobinuria, Fanconi's anemia, Blackfan-Diamond anemia, thalassemia major, sickle cell anemia, severe combined immunodeficiency, Wiskott-Aldrich syndrome, inborn errors of metabolism.

In some embodiment, organ injury may also be caused by ischemia. Ischemia may be a reversible or persisting (i.e. permanent) ischemia. Persisting ischemia is characterized in that the organ is inappropriately supplied by blood and, thus, hypoxic, even in a resting subject.

In some embodiments, organ injury may be caused by any form of chemical or physical agents, such as, drugs, environmental toxicants, or any other substance that contacts a subject and results directly or indirectly, in damage to the organ or tissue. Also included, is damage that results from successful therapeutic treatment of a subject, such as for example, the treatment which results in induction of organ's cell apoptosis (e.g. chemotherapy).

Thus, the present invention relates to a population of regulatory T which have been previously incubated with effective amount of a lymphotoxin alpha blocking agent and which expresses or not a TCR or a chimeric antigen receptor recognizing/binding to an autoantigen for use for regenerate tissue or organs.

In some embodiment, the organs or tissue is skeleton muscle, cardiac muscle, bone, skin or central nervous system.

Thus, the invention relates to a population of regulatory T which have been previously incubated with effective amount of a lymphotoxin alpha blocking agent and which expresses or not a TCR or a chimeric antigen receptor recognizing/binding to an autoantigen for use for regenerate skeleton muscle, cardiac muscle, bone, skin or central nervous system.

According to the invention, the populations of regulatory T cells of the invention are administered to the subject in the form of a pharmaceutical composition.

Accordingly, a further object of the present invention relates to a pharmaceutical composition comprising the population of regulatory T cells which has been pre-incubated with effective amount of lymphotoxin alpha blocking agent and/or the population of regulatory T cells which has been pre-incubated with effective amount of lymphotoxin alpha blocking agent and that it expresses a TCR or a chimeric antigen receptor which recognizes/binds to an autoantigen.

In some embodiment the lymphotoxin alpha blocking agent is a soluble lymphotoxin-β receptor (LTβR).

Thus, the present invention relates to a pharmaceutical composition comprising the population of regulatory T cells which has been pre-incubated with effective amount of soluble LTβR and/or the population of regulatory T cells which has been pre-incubated with effective amount of soluble LTβR and that it expresses a TCR or a chimeric antigen receptor which recognizes/binds to an autoantigen.

Typically, the populations of Tregs may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In one embodiment, the Tregs populations of the invention are administered by parenteral route. In a preferred embodiment, the Tregs populations of the invention are administered by intravenous route.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The populations of Tregs can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1. The adoptive transfer of LTα-/- Tregs protects from the severity of DSS-induced colitis. (A) Representative flow cytometry profiles of Foxp3 expression in purified splenic CD4+CD25+ cells from WT and LTα-/- mice. (B) Experimental setup: colitis was induced by the administration of 2% DSS in drinking water for 7 days followed by water only until day 11 in WT mice injected 2 days before with $2\times10^5$ WT or LTα-/- Tregs. Colon inflammation and CD4$^+$ T cell priming in mesenteric lymph nodes were analyzed at day 11 and day 4 of the protocol, respectively. (C) Body weight loss relative to the initial weight on day 0 of WT mice injected with $2\times10^5$ WT or LTα-/- Tregs. Data are derived from 3 independent experiment with 4 mice per group. (D) Disease activity index (DAI) was monitored during the course of DSS-induced colitis. (E) The histogram shows the histological score of the colon in both groups of mice.

FIG. 2. The adoptive transfer of WT Tregs pre-incubated with the soluble LTβR☐Fc fusion protein attenuates DSS-induced colitis. (A) Experimental setup: colitis was induced by the administration of 2% DSS in drinking water for 7 days followed by water only until day 11 in WT mice injected 2 days before with either 2×105 WT Tregs pretreated or not with LTβR-Fc protein or LTα-/- Tregs. Body weight was monitored every day and colon length was measured at day 11 of the protocol. (B) Body weight loss relative to the initial weight on day 0 of WT mice injected with either WT Tregs pre-incubated or not with the soluble LTβR-Fc fusion protein or LTα-/- Tregs. Data are derived from 1 independent experiment with 3-9 mice per group. (C) The histogram shows the colon length observed at the end of the experimental protocol.

FIG. 3. The suppressive signature of Treg cells is controlled by the LTα1β2/LTβR axis. (A) The expression level of Il10, Ebi3, Tgfb1, Ifn-γ, Gzmb and Fasl mRNAs was measured by qPCR in purified CD45.2 WT and LTα-/- Tregs from donor groups. (B) Purified WT Foxp3+CD4+ Tregs pre-incubated or not with a soluble LTβR-Fc fusion protein and co-cultured during 24 h with purified CD11c+ dendritic cells were analyzed for the expression level of Klrg1, Il10, Ebi3, Tgfb1, Gzmb and Fasl by qPCR.

EXAMPLE

Material & Methods
Mice
All mice—CD45.1 WT, CD45.1×CD45.2 WT, CD45.2 WT and CD45.2 LTα-/- mice—were on a pure C57BL/6 background and maintained under specific pathogen free conditions at the CIML (France). Standard food and water were given ad libitum. Males and females were used at the age of 6-8 weeks. All procedures involving animals have been performed in accordance with the institutional and ethical guidelines.
Treg Cell Isolation
Splenic Treg cells were isolated by scratching the spleen through a 70 μm mesh. Splenic red blood cells were lysed with lysis buffer (eBioscience). Before cell-sorting, CD4+ T cells were pre-enriched by depletion of CD8+ and CD19+ cells using anti-CD8a (clone 53.6.7) and anti-CD19 (clone 1D3) biotinylated antibodies with anti-biotin microbeads by AutoMACS (Miltenyi Biotech) via the deplete program. CD4+CD25+ Tregs were sorted using a FACSAriaIII cell sorter (BD).
DSS-Induced Colitis Experiments
Two days before the induction of colitis, WT recipient mice were injected i.v. with $2 \cdot 10^5$ CD4+CD25+ splenic Tregs sorted from WT or LTα-/- mice. The induction of colitis was assessed by given 2% DSS (Alfa Aesar) in drinking water for 7 days, followed by only water until sacrifice at d11. Body weight, rectal bleeding and stool consistency were monitored every day after DSS administration and used to determine the DAI.
In Vitro Co-Culture Assays
For co-culture assays, $2 \cdot 10^3$ cell-sorted total CD11c$^{hi}$ dendritic cells were co-cultured during 24 h at 37° C. with $10^4$ purified CD4$^+$CD25$^+$ Tregs that were or not pre-incubated during 1 h with a soluble LTβR-Fc recombinant protein (2 μg/ml; R&D systems).
Treg Cell Incubation with Soluble LTβR-Fc Protein in the DSS-Induced Colitis Model
2.105 CD4+CD25+ splenic Tregs purified from CD45.2 WT mice were pre-incubated or not with the soluble LTβR-Fc fusion protein (50 μg/ml; R&D Systems) for 30 min in culture medium (RPMI ThermoFisher with 10% FBS (Sigma Aldrich), 2 mM L-glutamine (ThermoFisher), 1 mM sodium pyruvate (ThermoFisher) and 2×10-5 M 2-mercaptoethanol (ThermoFisher)). Tregs were then adoptively transferred intravenously into CD45.2 WT recipients. 2.105 CD4+CD25+ splenic Tregs from LTα-/- mice were used as a control. Two days later, colitis was induced by given 2% DSS (Alfa Aesar) in drinking water for 7 days, followed by only water until sacrifice at d11. Body weight was monitored every day after DSS administration.

Figure 1B:
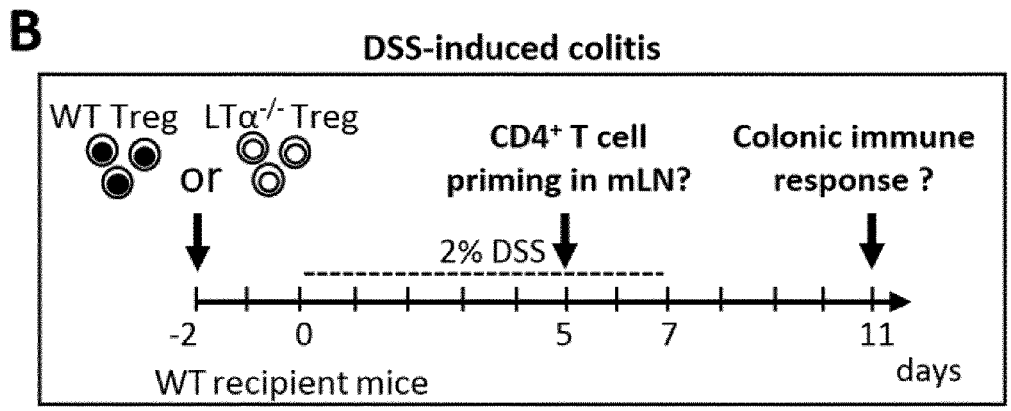
Figures 1C, 1D:
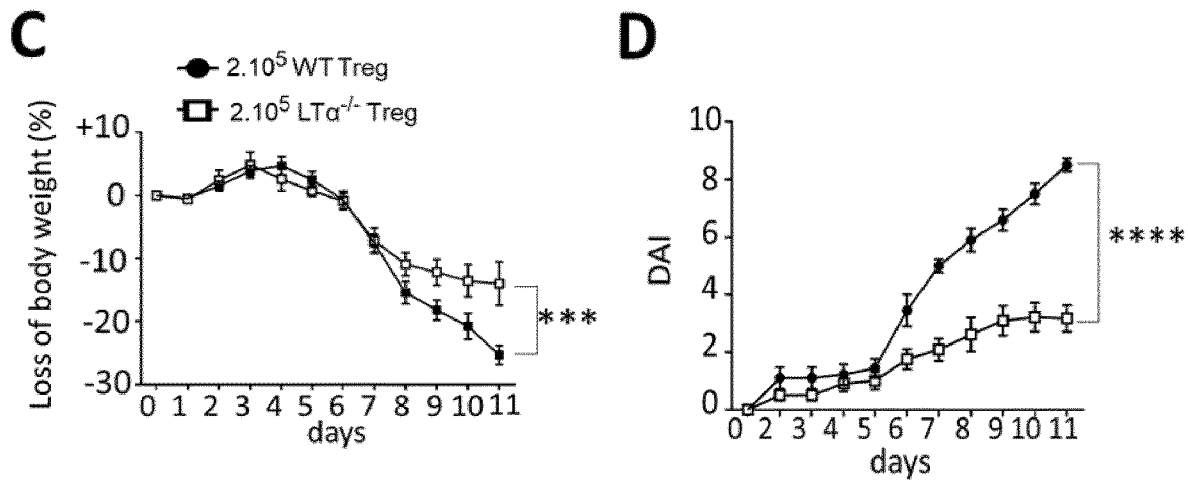
Figure 1E:
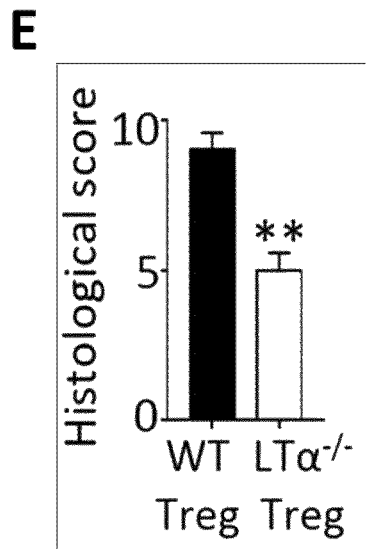

Flow Cytometry
Anti-CD4 (RM4.5) antibody was from BD. For intracellular staining with Foxp3 antibody, cells were fixed, permeabilized and stained with the Foxp3 staining kit according to the manufacturer's instructions (eBioscience). Stained cells were analyzed with FACSCanto II (BD) and data were analyzed using FlowJo software.
Quantitative RT-PCR
Total RNA was isolated with TRIzol (Invitrogen) and cDNA was synthesized with random oligo dT primers and Superscript II reverse transcriptase (Invitrogen). qPCR was performed with SYBR Premix Ex Taq master mix (Takara) on a ABI 7500 fast real-time PCR system (Applied Biosystem). Results were normalized to actin mRNA.
Statistical Analysis
Statistical significance was assessed with GraphPad Prism 6 software using unpaired Student's t test or Mann-Whitney test. The two-way Anova test with Bonferroni correction was used for the analysis of tumor growth, the loss of weight and DAI. *, $P<0.05$; , $P<0.01$; *, $P<0.001$; ****, $P<0.0001$. Normal distribution of the data was assessed using d'Agostino-Pearson omnibus normality test. Error bars represent mean±SEM.
Results
The Adoptive Transfer of LTα$^{-/-}$ Tregs Protects from Ulcerative Colitis
Given that LTα$^{-/-}$ Tregs highly express several genes implicated in Treg suppressive functions (data not shown), we evaluated whether the adoptive transfer of LTα$^{-/-}$ Tregs shows therapeutic benefits to protect from dextran sodium sulfate (DSS)-induced colitis. $2 \cdot 10^5$ CD4$^+$CD25$^+$ cells that predominantly contain Foxp3$^+$ Tregs (FIG. 1A) purified from WT or LTα$^{-/-}$ mice were injected into WT recipient mice two days before the induction of colitis with 2% DSS (FIG. 1B). We observed that mice injected with LTα$^{-/-}$ Tregs lost significantly less weight than those injected with WT Tregs (FIG. 1C). Moreover, the disease activity index (DAI), which combines stool consistency, rectal bleeding and weight loss was substantially less important in these mice (FIG. 1D). In accordance with the weight loss and DAI, these mice displayed less damages of the colonic epithelium (data not shown) and a reduced colitis histological score at the end of the experiment (FIG. 1E). We also observed a reduced expression of pro-inflammatory cytokines such as Il6, Ifnγ, Tnf-α, Il17A, Il1α and Il33 as well as of chemokines implicated in the recruitment of immune cells such as Ccl2 and Cxcl12 in colons of mice transferred with LTα$^{-/-}$ Tregs (data not shown). We further analysed the nature of colon-infiltrating immune cells by flow cytometry. Numbers of neutrophils, macrophages, dendritic cells, B cells and CD4$^+$ T cells were drastically reduced in mice transferred with LTα$^{-/-}$ Tregs compared to those transferred with WT Tregs (data not shown). A reduced infiltration of CD3$^+$ and B220$^+$ cells was confirmed on histological colon sections (data not shown). Numbers of Th1 and Th17 effector CD4$^+$ T cells were also reduced (data not shown). Consequently, Treg/Th1 and Treg/Th17 ratios were increased in the colon of mice transferred with LTα$^{-/-}$ Tregs (data not shown). We then assessed the potential of Ltα$^{-/-}$ Tregs to protect against colitis by reducing the number of adoptively transferred cells from $2 \cdot 10^5$ to $1 \cdot 10^5$ and then to $0.5 \cdot 10^5$ cells. We observed that $1 \cdot 10^5$ Ltα$^{-/-}$ Tregs still shows a better protection than $2 \cdot 10^5$ WT Tregs characterized by reduced weight loss (data not shown). Interestingly, $0.5 \cdot 10^5$ Ltα$^{-/-}$ Tregs show the same protective effect than $2 \cdot 10^5$ WT Tregs, indicating that Ltα$^{-/-}$ Tregs are ~4 times more suppressive in vivo than their WT counterparts.

We next further determined whether the adoptive transfer of LTα$^{-/-}$ Tregs inhibits CD4$^+$ T cell priming in mesenteric lymph nodes five days after the administration of DSS. Of note, we found that mice injected with LTα$^{-/-}$ Tregs already showed longer colon length and reduced colonic weight/length ratio at this time point, indicative of attenuated colon inflammation (data not shown). Strikingly, numbers of Th1 and Th17 effector CD4$^+$ T cells were substantially reduced in mesenteric lymph nodes of these mice (data not shown), indicating that LTα$^{-/-}$ Tregs inhibit the conversion of naïve CD4$^+$ T cells into effectors. Altogether, these data show that the adoptive transfer of LTα$^{-/-}$ Tregs protects from the development of ulcerative colitis by dampening colon inflammation and the priming of pathogenic CD4$^+$ T cells in mesenteric lymph nodes.

The Adoptive Transfer of WT Tregs Pre-Incubated with the Soluble LTβR☐Fc Fusion Protein Attenuates DSS-Induced Colitis.

Figure 2A:
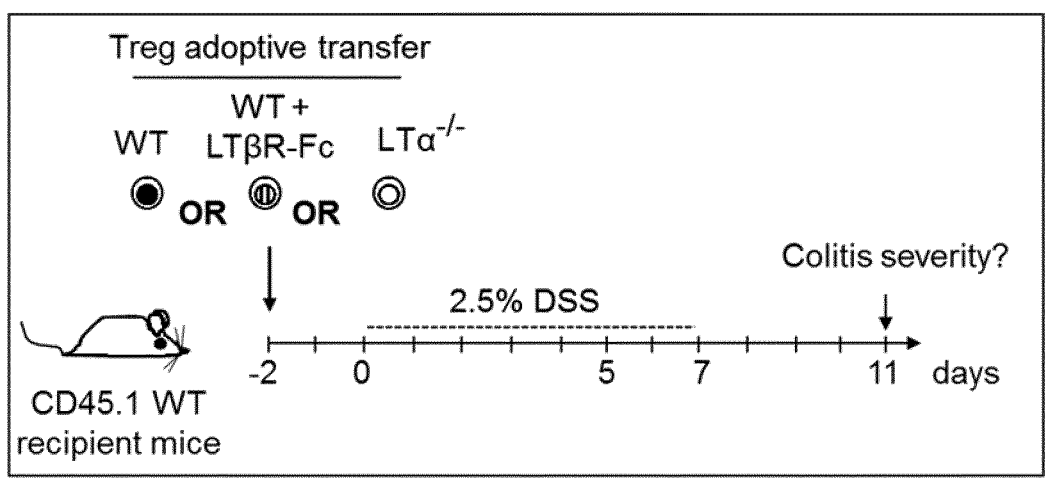
Figure 2B:
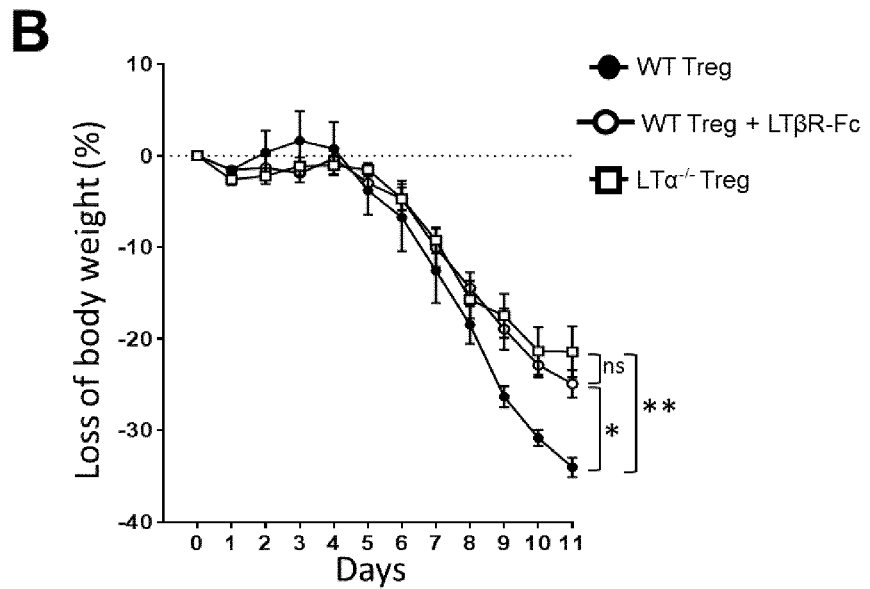
Figure 2C:
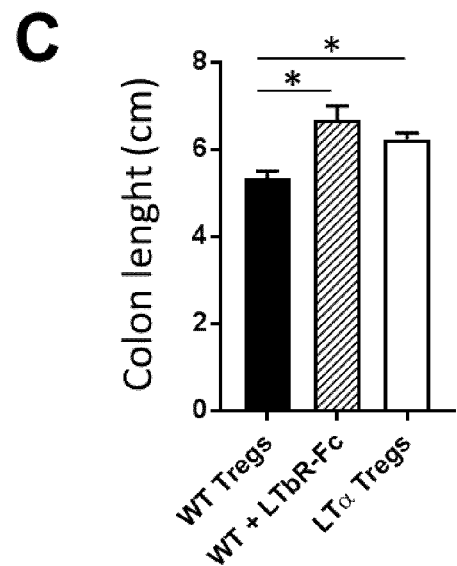

We next evaluated whether the adoptive transfer of Tregs pre-incubated with the soluble LTβR-Fc fusion protein shows therapeutic benefits to protect from dextran sodium sulfate (DSS)-induced colitis. 2·10$^5$ CD4$^+$CD25$^+$ cells that predominantly contain Foxp3$^+$ Tregs purified from LTα$^{-/-}$ or WT mice (FIG. 1A) were pre-incubated or not with the soluble LTβR-Fc fusion protein for 30 min in culture medium. Tregs were injected into WT recipient mice two days before the induction of colitis with 2% DSS (FIG. 2A). We observed that mice injected with Tregs pre-incubated with LTβR-Fc lost significantly less weight than those injected with WT Tregs and similarly to those injected with LTα$^{-/-}$ (FIG. 2B). Moreover, the colon of mice injected with Tregs pre-incubated with soluble LTβR-Fc is significantly longer than those injected with WT Tregs. However it is similar to the one of mice injected with LTα$^{-/-}$ (FIG. 2C).

Altogether, these data show that the adoptive transfer of WT Tregs pre-incubated with soluble LTβR-Fc protects from the development of ulcerative colitis as effectively as LTα$^{-/-}$ Tregs.

LTα Expression in Hematopoietic Cells and LTα1β2/LTβR Axis Negatively Control the Suppressive Signature of Treg Cells Because LTα$^{-/-}$ mice show a disorganized thymic and splenic microenvironment, we analysed the contribution of non-hematopoietic stromal cells in the highly immunosuppressive phenotype of LTα$^{-/-}$ Tregs. For this, we generated bone marrow (BM) chimeras in which lethally irradiated CD45.2 WT or LTα$^{-/-}$ recipient mice were reconstituted with WT BM cells from CD45.1 congenic mice (WT CD45.1: WT and WT CD45.1: LTα$^{-/-}$ mice, respectively). Six weeks after BM transplantation, CD4$^+$CD25$^+$ Treg cells of CD45.1 donor origin were cell-sorted from the spleen and analysed for the expression of several genes associated with Treg effector function (data not shown). Similar frequencies and numbers of Foxp3$^+$ Tregs were observed in both groups of mice (data not shown). Furthermore, the expression of several genes such as Klrg1, Tgfb, Gzmb and Fasl was similar in both groups of mice, indicating that non-hematopoietic cells are not implicated in the highly suppressive signature of Tregs observed in LTα$^{-/-}$ mice (data not shown).

Figure 3A:
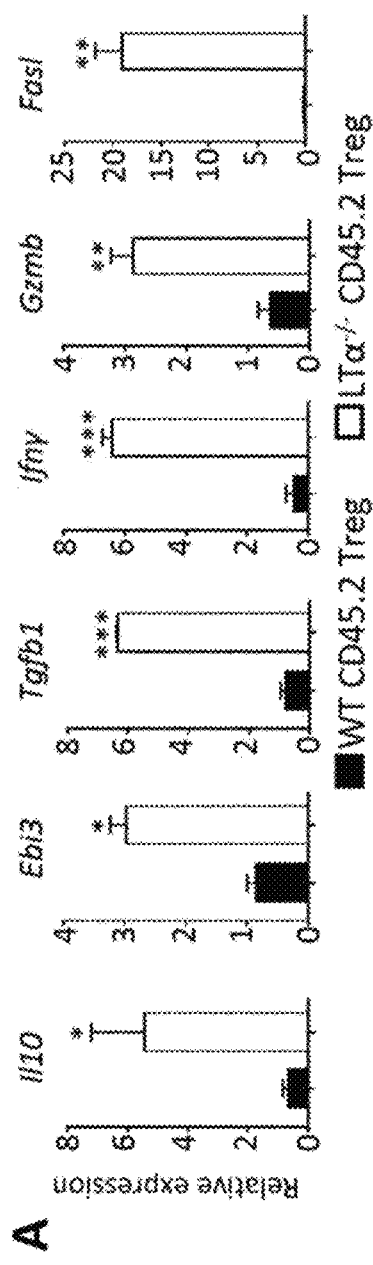

We next determined the respective contribution of the hematopoietic compartment by generating mixed bone marrow chimaeras in which lethally irradiated CD45.1×CD45.2 WT recipient mice were reconstituted with BM cells (50:50) from WT CD45.1 and WT CD45.2 (WT donor group), or WT CD45.1 and LTα$^{-/-}$ CD45.2 (LTα$^{-/-}$ donor group) (data not shown). Six weeks later, we found increased frequencies and numbers of CD4$^+$Foxp3$^+$ Tregs derived from LTα$^{-/-}$ CD45.2 BM cells compared to those derived from WT CD45.2 BM cells in the spleen (data not shown). Strikingly, purified LTα$^{-/-}$ CD45.2 Tregs showed increased expression of Il10, Ebi3, Tgfb1, Ifng, Gzmb and Fasl genes compared to WT CD45.2 Tregs (FIG. 3A). These data indicate that the expression of LTα in hematopoietic cells negatively controls the immunosuppressive signature of Treg cells.

Figure 3B:
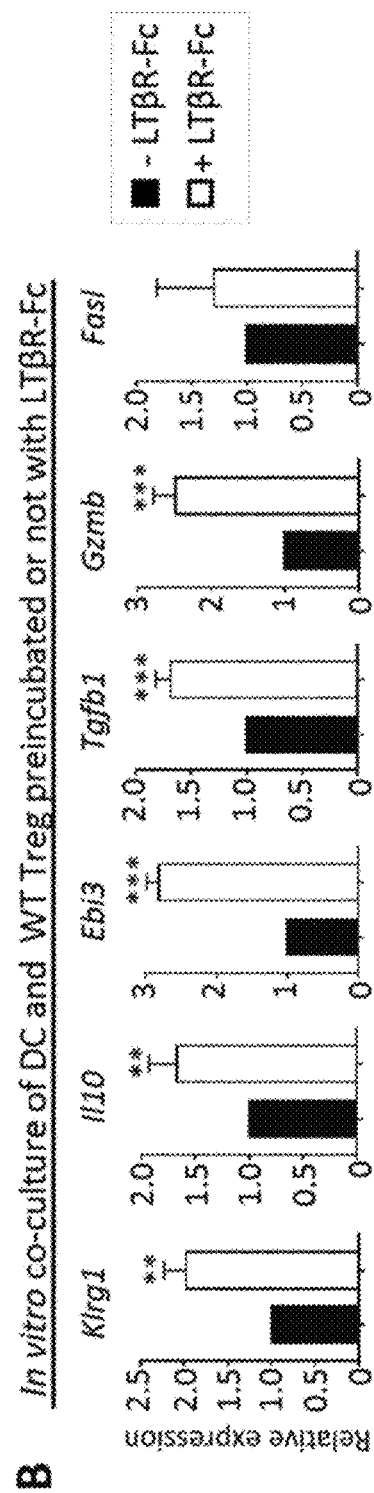

Since we observed that Tregs express LTα, as a membrane anchored LTα1β2 heterocomplex (data not shown), we assessed the contribution of LTα1β2/LTβR axis in controlling the suppressive signature of Tregs. In particular, we analyzed whether blocking LTα1β2/LTβR interactions between Tregs and dendritic cells impacts the suppressive signature of Treg cells. For this, purified WT CD4$^+$CD25$^+$ Tregs pre-incubated or not with a soluble LTβR-Fc fusion protein were co-cultured with purified CD11 dendritic cells. Interestingly, Tregs that were pre-incubated with LTβR-Fc upregulated the expression of several genes associated with Treg suppressive function such as Klrg1, Il10, Ebi3, Tgfb1, Gzmb and Fasl compared to un-pretreated Tregs (FIG. 3B). These data thus indicate that LTα1β2/LTβR interactions between Tregs and dendritic cells negatively regulate the suppressive signature of Tregs.

LTα Expression is Conserved in Human Tregs Derived from Peripheral Blood

We next assessed whether LTα expression is conserved in human Tregs derived from peripheral blood of female and male healthy donors. Foxp3$^+$CD4$^+$ Tregs were classically identified as CD4$^+$CD25$^+$CD127$^{lo}$ cells. Intracellular LTα protein (data not shown) and the cell-surface LTα1β2 heterocomplex (data not shown) were substantially detected by flow cytometry in Tregs of all donors analyzed, indicating that this expression is conserved in mice to human.

DISCUSSION

Several studies have identified numerous molecules implicated in the positive regulation of Treg cell development and function. In contrast, few reports have described signals that negatively regulate Treg function. Here, by analyzing distinct T cell populations endowed with regulatory properties, we found that Foxp3+ Tregs substantially express Lta, as a membrane anchored LTα1β2 heterocomplex. Similarly to LTβR$^{-/-}$ mice, LTα$^{-/-}$ mice do not show any obvious defect in CD4$^+$Foxp3$^+$ Treg cell development in the thymus. However, the signature of genes associated with suppressive functions was greatly enhanced both in LTα$^{-/-}$ Tregs, indicating that LTα, and more precisely the LTα1β2/LTβR interactions between Tregs and dendritic cells negatively regulates their immunosuppressive signature.

Interestingly, we have previously demonstrated that the adoptive transfer of LTα$^{-/-}$ Tregs protects from DSS-induced colitis (FIG. 1) and treats from IBD more efficiently than WT Tregs. This was reflected by a reduced body weight loss, a higher colon length and a reduced histological score in mice transferred with LTα$^{-/-}$ Tregs compared to mice injected with WT Tregs. Furthermore, we observed that LTα$^{-/-}$ Tregs substantially reduce colon inflammation and the infiltration of inflammatory immune cells. In the DSS-induced colitis model, we found that the transfer of LTα$^{-/-}$ Tregs before the induction of colitis reduces the priming and/or expansion of Th1 and Th17 pathogenic cells in mesenteric lymph nodes. Importantly, the ratios Treg/Th1 and Treg/Th17 were increased in the colon in both the DSS-induced colitis and IBD models, suggesting that Tregs can also exert their suppressive effects locally in this tissue.

By their ability to suppress colon inflammation, the adoptive transfer of LTα$^{-/-}$ Tregs also attenuates the development of CAC, which is known to be promoted by chronic inflammation. Altogether, these data indicated that compared to their WT counterparts, LTα$^{-/-}$ Tregs show a higher capacity to treat colitis and protect from both colitis and CAC development. We also revealed that LTα1β2/LTβR interactions between Tregs and dendritic cells, particularly Sirpα$^+$ conventional dendritic cells and plasmacytoid dendritic cells, negatively control the suppressive signature of Treg cells, suggesting that a direct cell contact with antigen-present cells regulates Treg suppressive activity.

Herein, we show that the adoptive transfer of WT Tregs pre-incubated with soluble LTβR-Fc protects from the development of ulcerative colitis as effectively as LTα$^{-/-}$ Tregs (FIG. 2B-C). Furthermore, WT Tregs pre-incubated with soluble LTβR-Fc displays a similar suppressive signature than the LTα$^{-/-}$ Tregs (FIG. 3). Therefore, the adoptive transfer of WT Tregs pre-incubated with soluble LTβR-Fc is expected to not only protect from DSS-induced colitis but also treat from IBD and attenuate the development of CAC as effectively as the adoptive transfer of LTα$^{-/-}$ Tregs.

REFERENCES

Throughout this application, various references describe the state of the art to which this invention pertains. The disclosures of these references are hereby incorporated by reference into the present disclosure.

1. Sakaguchi, S., et al. (2008). Regulatory T cells and immune tolerance. *Cell* 133, 775-787.
2. Dhamne, C. et al. (2013). Peripheral and thymic foxp3(+) regulatory T cells in search of origin, distinction, and function. *Front Immunol* 4, 253.
3. Fontenot, J. D. et al. (2005). Developmental regulation of Foxp3 expression during ontogeny. *The Journal of experimental medicine* 202, 901-906.
4. Brunkow, M. E. et al. (2001). Disruption of a new forkhead/winged-helix protein, scurfin, results in the fatal lymphoproliferative disorder of the scurfy mouse. *Nature genetics* 27, 68-73.
5. Bennett, C. L. et al. (2001). The immune dysregulation, polyendocrinopathy, enteropathy, X-linked syndrome (IPEX) is caused by mutations of FOXP3. *Nature genetics* 27, 20-21.
6. Maloy, K. J. et al. (2003). CD4+CD25+ T(R) cells suppress innate immune pathology through cytokine-dependent mechanisms. *The Journal of experimental medicine* 197, 111-119.
7. Szanya, V. et al. (2002). The subpopulation of CD4+CD25+ splenocytes that delays adoptive transfer of diabetes expresses L-selectin and high levels of CCR7. *Journal of immunology* 169, 2461-2465.
8. McGeachy, M. J. et al. (2005). Natural recovery and protection from autoimmune encephalomyelitis: contribution of CD4+CD25+ regulatory cells within the central nervous system. *Journal of immunology* 175, 3025-3032.
9. Presser, K. et al. (2008). Coexpression of TGF-beta1 and IL-10 enables regulatory T cells to completely suppress airway hyperreactivity. *Journal of immunology* 181, 7751-7758.
10. Waldner, M. J., and Neurath, M. F. (2009). Colitis-associated cancer: the role of T cells in tumor development. *Semin Immunopathol* 31, 249-256.
11. Riley, J. L. at al. (2009). Human T regulatory cell therapy: take a billion or so and call me in the morning. *Immunity* 30, 656-665.
12. Bluestone, J. A., et al. (2015). Type 1 diabetes immunotherapy using polyclonal regulatory T cells. *Sci Transl Med* 7.
13. Desreumaux, P. et al. (2012). Safety and efficacy of antigen-specific regulatory T-cell therapy for patients with refractory Crohn's disease. *Gastroenterology* 143.
14. Di Ianni, M. et al. (2011). Tregs prevent GVHD and promote immune reconstitution in HLA-haploidentical transplantation. *Blood* 117, 3921-3928.

The invention claimed is:

1. An ex vivo method for stimulating regulatory T cells immunosuppressive activity, said method comprising:
   i. obtaining a biological sample from a subject;
   ii. isolating regulatory T cells from said sample;
   iii. expanding the regulatory T cells in vitro;
   iv. incubating the regulatory T cells with an amount of lymphotoxin alpha blocking agent sufficient to block LTα1β2/LTβR or LTα2β1/LTβR interactions.

2. The method according to claim 1 wherein the biological sample is a blood sample.

3. A method of treating an autoimmune disorder in a subject in need thereof comprising administering to the subject a therapeutically effective amount of a population of regulatory T cells which has been previously incubated with an amount of a lymphotoxin alpha blocking agent sufficient to increase the suppressive activity of the regulatory T cells.

4. The method according to claim 3, wherein the autoimmune disorder is inflammatory bowel disease.

5. A method of treating inflammation-associated cancer or allergy in a subject in need thereof comprising administering to the subject a therapeutically effective amount of a population of regulatory T cells which has been previously incubated with an amount of a lymphotoxin alpha blocking agent sufficient to increase the suppressive activity of the regulatory T cells.

6. The method according to claim 5, wherein the inflammation-associated cancer is colitis-associated cancer.

7. A method of treating immune reactions against molecules that are exogenously administered or immune reactions against a grafted tissue or grafted cells in a subject in need thereof comprising administering to the subject a therapeutically effective amount of a population of regulatory T cells which has been previously incubated with an amount of a lymphotoxin alpha blocking agent sufficient to increase the suppressive activity of the regulatory T cells.

* * * * *

SEQUENCE LISTING

<160> NUMBER OF SEQ ID NOS: 2

<210> SEQ ID NO 1
<211> LENGTH: 197
<212> TYPE: PRT
<213> ORGANISM: Homo sapiens

<400> SEQUENCE: 1

```
Gln Ala Val Pro Pro Tyr Ala Ser Glu Asn Gln Thr Cys Arg Asp Gln
1               5                   10                  15

Glu Lys Glu Tyr Tyr Glu Pro Gln His Arg Ile Cys Cys Ser Arg Cys
            20                  25                  30

Pro Pro Gly Thr Tyr Val Ser Ala Lys Cys Ser Arg Ile Arg Asp Thr
        35                  40                  45

Val Cys Ala Thr Cys Ala Glu Asn Ser Tyr Asn Glu His Trp Asn Tyr
    50                  55                  60

Leu Thr Ile Cys Gln Leu Cys Arg Pro Cys Asp Pro Val Met Gly Leu
65                  70                  75                  80

Glu Glu Ile Ala Pro Cys Thr Ser Lys Arg Lys Thr Gln Cys Arg Cys
                85                  90                  95

Gln Pro Gly Met Phe Cys Ala Ala Trp Ala Leu Glu Cys Thr His Cys
            100                 105                 110
```

```
Glu Leu Leu Ser Asp Cys Pro Pro Gly Thr Glu Ala Glu Leu Lys Asp
            115                 120                 125

Glu Val Gly Lys Gly Asn Asn His Cys Val Pro Cys Lys Ala Gly His
    130                 135                 140

Phe Gln Asn Thr Ser Ser Pro Ser Ala Arg Cys Gln Pro His Thr Arg
145                 150                 155                 160

Cys Glu Asn Gln Gly Leu Val Glu Ala Ala Pro Gly Thr Ala Gln Ser
                165                 170                 175

Asp Thr Thr Cys Lys Asn Pro Leu Glu Pro Leu Pro Pro Glu Met Ser
            180                 185                 190

Gly Thr Met Leu Met
            195
```

<210> SEQ ID NO 2
<211> LENGTH: 421
<212> TYPE: PRT
<213> ORGANISM: Artificial Sequence
<220> FEATURE:
<223> OTHER INFORMATION: Synthetic Baminercept

<400> SEQUENCE: 2

```
Ala Val Pro Pro Tyr Ala Ser Glu Asn Gln Thr Cys Arg Asp Gln Glu
1               5                   10                  15

Lys Glu Tyr Tyr Glu Pro Gln His Arg Ile Cys Cys Ser Arg Cys Pro
            20                  25                  30

Pro Gly Thr Tyr Val Ser Ala Lys Cys Ser Arg Ile Arg Asp Thr Val
            35                  40                  45

Cys Ala Thr Cys Ala Glu Asn Ser Tyr Asn Glu His Trp Asn Tyr Leu
    50                  55                  60

Thr Ile Cys Gln Leu Cys Arg Pro Cys Asp Pro Val Met Gly Leu Glu
65                  70                  75                  80

Glu Ile Ala Pro Cys Thr Ser Lys Arg Lys Thr Gln Cys Arg Cys Gln
                85                  90                  95

Pro Gly Met Phe Cys Ala Ala Trp Ala Leu Glu Cys Thr His Cys Glu
            100                 105                 110

Leu Leu Ser Asp Cys Pro Pro Gly Thr Glu Ala Glu Leu Lys Asp Glu
            115                 120                 125

Val Gly Lys Gly Asn Asn His Cys Val Pro Cys Lys Ala Gly His Phe
    130                 135                 140

Gln Asn Thr Ser Ser Pro Ser Ala Arg Cys Gln Pro His Thr Arg Cys
145                 150                 155                 160

Glu Asn Gln Gly Leu Val Glu Ala Ala Pro Gly Thr Ala Gln Ser Asp
                165                 170                 175

Thr Thr Cys Lys Asn Pro Leu Glu Pro Leu Pro Pro Glu Met Ser Gly
            180                 185                 190

Thr Met Val Asp Lys Thr His Thr Cys Pro Pro Cys Pro Ala Pro Glu
        195                 200                 205

Leu Leu Gly Gly Pro Ser Val Phe Leu Phe Pro Pro Lys Pro Lys Asp
        210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270
```

-continued

```
Ser Thr Tyr Arg Val Val Ser Val Leu Thr Val Leu His Gln Asp Trp
        275                 280             285

Leu Asn Gly Lys Glu Tyr Lys Cys Lys Val Ser Asn Lys Ala Leu Pro
    290             295             300

Ala Pro Ile Glu Lys Thr Ile Ser Lys Ala Lys Gly Gln Pro Arg Glu
305             310             315                 320

Pro Gln Val Tyr Thr Leu Pro Pro Ser Arg Asp Glu Leu Thr Lys Asn
            325             330             335

Gln Val Ser Leu Thr Cys Leu Val Lys Gly Phe Tyr Pro Ser Asp Ile
        340             345             350

Ala Val Glu Trp Glu Ser Asn Gly Gln Pro Glu Asn Asn Tyr Lys Thr
        355             360             365

Thr Pro Pro Val Leu Asp Ser Asp Gly Ser Phe Phe Leu Tyr Ser Lys
    370             375             380

Leu Thr Val Asp Lys Ser Arg Trp Gln Gln Gly Asn Val Phe Ser Cys
385             390             395             400

Ser Val Met His Glu Ala Leu His Asn His Tyr Thr Gln Lys Ser Leu
            405             410             415

Ser Leu Ser Pro Gly
            420
```